United States Patent [19]

Eckstein et al.

[11] Patent Number: 4,527,293
[45] Date of Patent: Jul. 9, 1985

[54] HYDROGEL SURFACE OF UROLOGICAL PROSTHESIS

[75] Inventors: Eugene C. Eckstein; Norman L. Block, both of Miami; Jacob Kline, Coral Gables; Leonard Pinchuk, Miami, all of Fla.

[73] Assignee: University of Miami, Coral Gables, Fla.

[21] Appl. No.: 495,698

[22] Filed: May 18, 1983

[51] Int. Cl.³ ............... A61M 25/00; C08F 220/54; C08J 7/04

[52] U.S. Cl. ..................... 623/12; 604/266; 424/32; 424/81; 523/113; 524/916

[58] Field of Search ............ 3/1; 523/103, 105, 113; 524/916; 427/3; 428/424.4; 424/16, 32, 81; 604/264, 266

[56] References Cited

U.S. PATENT DOCUMENTS

| | | |
|---|---|---|
| 2,976,576 | 3/1961 | Wichterle et al. |
| 3,220,960 | 11/1965 | Wichterle et al. |
| 3,520,949 | 7/1970 | Shepard et al. |
| 3,566,874 | 3/1971 | Shepard et al. |
| 3,607,848 | 9/1971 | Stoy |
| 3,660,561 | 2/1972 | Shepard et al. |
| 3,663,288 | 5/1972 | Miller |
| 3,695,921 | 10/1972 | Shepard et al. |
| 3,767,790 | 10/1973 | Guttag |
| 3,941,858 | 3/1976 | Shepard et al. |
| 3,943,045 | 3/1976 | Cordrey et al. |
| 3,997,482 | 12/1976 | Turkova et al. |
| 4,021,382 | 5/1977 | Stoy et al. |
| 4,045,547 | 8/1977 | LeBoeuf et al. |
| 4,056,496 | 11/1977 | Mancini et al. |
| 4,074,039 | 2/1978 | Lim et al. |
| 4,076,921 | 2/1978 | Stol et al. |

OTHER PUBLICATIONS

Block et al., Trans. Am. Soc. Aftif. Intern. Organs., 23, (1977), 367.
Levowitz et al., Trans. Am. Soc. Aftif. Intern. Organs., 14, (1968), 82.
Kocvara et al., J. Biomed. Mater. Res., vol. 1, (1967), 325.
Kocvara et al., J. Biomed. Mater. Res., vol. 2, (1968), 489.
Leray, Evr. Surg. Res., 8, Supp. 2, No. 134, 129.
Sprinel et al., Calc. Tiss. Res., 13, (1973), 63.
Cerny et al., Scripta Medica, 13, (1973), 63.
Smahel et al., Acta Chirvgiae Plasticae, 13, 4, (1971), 193.
Kronman et al., Biomat., Med. Dev. Art. Org., 7(2), (1974), 299.
Ratner et al., in "Hydrogels for Medical and Related Applications", ACS Symposium Series, vol. 31, (1976), 1.
NTIS Polysciences, Inc. Annual Report, 1972.
Kline, J. et al., "Development of a Total Prosthetic Urinary Bladder", Trans. Am. Soc. Internal. Organs, 24:254, 1978.
Pinchuk, L., "Development of a Totally Implantable Artificial Urinary Bladder, Generation IV, Hydrogel Coated", University of Miami, MS. thesis, 1979.
Coleman, D. L., "Mineralization of Blood Pump Bladders", Trans. Am. Soc. Internal. Organs, 27:708, 1981.
Jansen, B. and Ellinghorst, G., "Modification of Polyetherurthane for Biomedical Application by Radiation Induced Grafting, II, Water Sorption, Surfact Properties, and Protein Absorption of Grafted Films", J. Biomedical Materials Res., 18:655, 1984.
NTIS Polysciences, Inc. Annual Report, 1976.
Gregonis et al., in "Hydrogels for Medical and Related Applications", ACS Symposium Series, vol. 31, (1976), 88.
Ilavsky et al., J. Appl. Pol. Sci., 23, (1979), 2073.

Primary Examiner—Richard J. Apley
Assistant Examiner—Gregory Beaucage
Attorney, Agent, or Firm—Cushman, Darby & Cushman

[57] ABSTRACT

Disclosed is a urological device comprising a polymeric prosthesis coated on its surface by a grafted or interpenetrated hydrogel copolymer comprising 2-hydroxyethyl methacrylate, methacrylic acid, and a crosslinking agent, wherein each constituent of said copolymer is present in an amount selected from a defined range of mole fraction %. The hydrogel exhibits a shrink/swell behavior which varies with changing urine composition such that the polymer undergoes swelling and collapse in rapid response to said change and thereby prevents calcium encrustation. Also disclosed is a method for making the device.

23 Claims, 1 Drawing Figure

HYDROGEL SURFACE OF UROLOGICAL PROSTHESIS

FIELD OF THE INVENTION

This invention relates to artificial urological prostheses, such as bladders, ureters, etc. which are coated on urine contacting surfaces with a thin layer of a hydrogel copolymer formed from 2-hydroxyethyl methacrylate (HEMA), methacrylic acid (MAA), and a cross-linking agent.

BACKGROUND OF THE INVENTION

Research in the area of prosthetic devices formed from polymeric materials has been vigorous, generally having the espoused purpose of locating polymers which are compatible in physiological environments and which can be used to form prosthetic devices which maintain their structural integrity over long periods of time. With respect to research in the area of urological prostheses, however, a thorny problem arises in that, due to the high salt content of urinary fluids, calcium encrustation of polymeric prostheses takes place and builds up over time such that the bladder is "choked off", or scaled such that the use of these devices for long term periods has been generally foreclosed. The present invention remedies this drawback by grafting to or interpenetrating with the surface of any prosthetic urological device a thin layer of a hydrogel copolymer comprised of poly (2-hydroxyethyl methacrylate), pHEMA. The unique manner in which artificial bladders constructed in accordance with the principles of the present invention will be subsequently detailed.

Hydrogel prostheses made of pHEMA have demonstrated resistance to calcification in the urinary tract (Block et al, Trans. Amer. Soc. Art. Int. Organs., 23, 367, 1977; Kocvara et al, J. Biomed. Mat. Res., 2, 489, 1967; Levowitz et al, Trans. Amer. Soc. Art. Int. Organs., 14, 82, 1968). Recent data suggests that the methacrylic acid, MAA, content in these gels plays a critical role in their urine compatibility. It is also well known that the equilibrium water content and other properties of the gel change significantly according to MAA content (Ilavsky et al, J. Appl. Polym. Sci., 23, 2073, 1979).

Articles used in medical applications which have been fabricated in bulk from hydrogels such as copolymers of pHEMA and MAA are known. For example, U.S. Pat. No. 2,976,576 to Wichterle discloses shaped three-dimensional articles formed wholly of a polymer which may be fabricated in part from a glycol monomethacrylate copolymerized with MAA. The advantages pointed out derive chiefly from the fact that the polymers are resistant to chemical attack and have colloidal properties making them compatible with living tissue and membranes. The polymer is described as having the capability of swelling in solution. Similarly, U.S. Pat. No. 3,220,960, also to Wichterle, discloses cross-linked hydrophilic polymers compatible with physiological environments and articles made therefrom, which polymers form hydrogels that are capable of being elastically deformed by swelling with water.

U.S. Pat. No. 3,520,949 to Shepherd discloses hydrophilic polymers based on hydroxyalkyl methacrylates used as flavor or essence carriers and discloses that the polymers have reversible fluid absorption properties. The polymers are stated to be chemically and physically inert. U.S. Pat. No. 3,566,874, also to Shepherd, a continuation-in-part of the aforementioned U.S. Pat. No. 3,520,949, discloses catheters coated with polymers which may be fabricated from lower hydroxyalkyl acrylates and which may be used as a carrier for an antibiotic or germicide to reduce the risk of infection.

U.S. Pat. No. 4,076,921 to Stol discloses glycol acrylates or glycol methacrylates which may be copolymerized with methacrylic acid and crosslinked with glycol dimethacrylates. Use of the polymer as a prosthetic material is noted.

None of the preceeding documents disclose, however, that calcium encrustation of the surface of a urinary bladder or other urinary tract prostheses can be effectively dealt with on a continuous and ongoing basis over long periods of time in the manner developed by the present inventors. None of these references provide details of the effects of low levels of MAA, i.e. less than 4 mole fraction %, on the swelling behavior of gels having a crosslinker content less than 0.5%. For that matter, much of the research in the area of hydrogels has been bottomed on the knowledge that swelling behavior in largely dependent on the amount of ionizable species (e.g. MAA) in the polymer. Much of this research, therefore, can perhaps be characterized by the attitude that if "some is good, more is better".

Further, the present inventors have discovered that a phenomenon known as "polymer collapse" can be used to great advantage to solve the problem of calcium encrustation by grafting or surface interpenetrating a thin layer of a pHEMA-MAA cross-linked copolymer system onto a substantially physically and chemically inert substance used to form a urological prothesis. The term "polymer collapse" refers to the phenomenon whereby hydrogels are characterized by certain equilibrium volumes depending on the aqueous environment into which they are placed. As environmental conditions change, e.g., salt concentration, pH, etc., this equilibrium volume also changes with time. The term "polymer collapse" refers only to the fact that a hydrogel may be swollen depending upon its aqueous environment, but does not imply anything with respect to temporal suddenness, i.e. the amount of time which is required for the gel equilibrium volume to change.

Recent research on polymer collapse by Tanaka et al (*Scattering Techniques Applied to Supramolecular and Nonequilibrium Systems,* Ed. S-H. Chin, B. Chu, R. Nossal., Plenum, New York 1981) shows that the gel volume is the result of three constituent forces that set the osmotic pressure within the gel. These forces are (1) the rubber-like elasticity, (2) polymer-polymer affinity and (3) hydrogen-ion pressure. Tanaka et al showed that when environmental factors such as pH, electrolyte or solvent concentration are plotted against a property of a gel such as swelling or water content, the curve describing the transition of the polymer from a swollen state to a contracted state, or vice-versa, may be continuous, corresponding to shrinkage, or discontinuous corresponding to collapse of the gel. These events pertain, as previously described, to the equilibrium volume of the gel and not to the time required to reach equilibrium swelling. As volume changes are tied to diffusive rearrangement of the polymer structure, changes of state can be quite lengthy for bulk gels. Experiments show that bulk gels with normal levels of crosslinker (greater than 0.5%) that are 2–3 mm in thickness may require as long as 2–3 days at 40° C. to reach equilibrium. Similarly sized bulk gels doped with MAA and with smaller levels of crosslinker require only 2–3 hours at 40° C. to reach equilibrium. The inventors have now discovered that significantly faster changes occur for surface zones or for thin grafted layers which, having thicknesses on the orders of microns, can respond to local environmental changes within seconds.

SUMMARY OF THE INVENTION

The present inventors have discovered that hydrogels containing concentrations of HEMA, MAA and crosslinker selected from critical ranges may be fabricated so as to demonstrate equilibrium swelling differences of several hundred percent within the narrow range of urine composition. The invention is further predicated on the discovery that gels fabricated with small amounts of MAA and with low crosslinker content denonstrate a reversible shrink/swell behavior that is responsive to changes in electrolyte, pH, or urea content of urine. Within the limits of urine composition, the extent of this shrink/swell behavior may be as large as several hundred percent and can occur quite rapidly as a response to small changes in the local environment. The solids content of the gel may vary between 20% and 60%. The crosslinker employed is tetraethylene glycol dimethacrylate (TEGDMA).

In addition to the discovery that hydrogels formulated in accordance with this invention undergo unexpectedly large swelling changes relative to the much smaller dimensional changes of pure HEMA when placed in different chemical enviroments, the inventors have further discovered that these dramatic changes can be controlled by doping pure HEMA monomer (or HEMA monomer having known small impurity concentrations) with appropriate MAA and crosslinker content. Thus, by precisely ascertaining the levels of MAA and crosslinker in the hydrogel layer, its performance as a biomaterial can be evaluated.

As noted above, bulk hydrogels exhibit volume swelling changes which may amount to as much as several hundred or even several thousand percent of the unswollen gel volume. A urological prosthesis fabricated in bulk from such a material would be useless for medical applications because such drastic changes in an organ the size of, e.g. a bladder could obviously not be tolerated.

The inventors, by contrast, have combined the phenomenon of polymer collapse with the use of very thin hydrogel layers to speed up the collapse event relative to that obtainable with the bulk gel. By grafting a thin layer of a hydrogel onto the urine-contacting surface of a prosthetic device, e.g. a bladder, which is itself physically substantially unresponsive to changes in the local enviroment, a bladder may be fabricated which exhibits very fast (on the order of a couple of seconds) response times to local environmental changes without the entire bladder drastically changing the amount of volume it occupies within the human body. The hydrogel layer, when fabricated according to the invention, presents a mobile surface which, in essence, represents a physiological spring-powered machine that is "cocked and released" by changes in the external urine composition. Any calcium which may have started to solidify onto the surface of the bladder is believed to be abruptly and efficiently thrown off or descaled to be carried away. The constant and cyclical swelling and shrinkage of the hydrogel surface thus maintains the prosthetic device regions coated therewith in a calcium-free condition.

The present invention derived from considering the biochemistry of the environment within the urinary tract. Such consideration indicated that there are potent events which could change the magnitude of the polymer-polymer affinity and the hydrogen-ion pressure in ionic gels. It is believed that these are in large part the changes which cause the polymer to undergo drastic volume changes.

First, it is known that the composition of urine changes daily depending upon food intake and metabolic activity of the individual (White et al, Principles of Biochemistry, McGraw Hill, New York, pgs. 1064–1084, 1978). It is also known that electrolytes and urea form a large fraction of the solute content in urine, and that urea, the end product of protein catabolism, is a potent swelling agent for hydrogels (Refojo, J. Polym. Sci., A-1, 5, 3103, 1967; Ratner et al, J. Polym. Sci., A-1, 10, 2425, 1972). Urea may disrupt the secondary structure of the gel by interacting with hydrogen-bonded hydroxyl groups, thereby facilitating swelling of the gel (Ratner et al, supra), and it is in this sense that urea can strongly alter the polymer-polymer affinity of the gel.

Second, the pH of urine varies between 4 and 9 (White et al, supra) and, most importantly, the pKa of MAA is within this range. At low pH, the hydrogen ion remains bound to the acid moiety on MAA and the gel remains collapsed. As the alkalinity of the solution is increased, the proton dissociates, resulting in a larger hydrogen-ion pressure, increased electrorepulsion, and a swollen gel (Tanaka et al, supra). Electrolytes in urine, i.e., calcium, sodium, and potassium, shield the ionic charge on MAA and tend to collapse the swollen gel.

Moreover, the extent of swelling and collapse are limited by the rubber-like elasticity of the molecular lattice. The degree of crosslinking in the gel and the molecular weight of the polymer are largely responsible for limiting the rubber-like elasticity of the polymer lattice. The equilibrium state of the gel represents a balance point among the rubber-like elasticity, effects of the polymer-polymer affinity, and the hydrogen-ion pressure. Thus, by employing the principles of this invention to control the amounts of crosslinker and ionizable species, a gel may be fabricated which demonstrates equilibrium swelling indifferences of several hundred percent within the narrow range of urine composition.

DETAILED DISCUSSION

Figure 1:
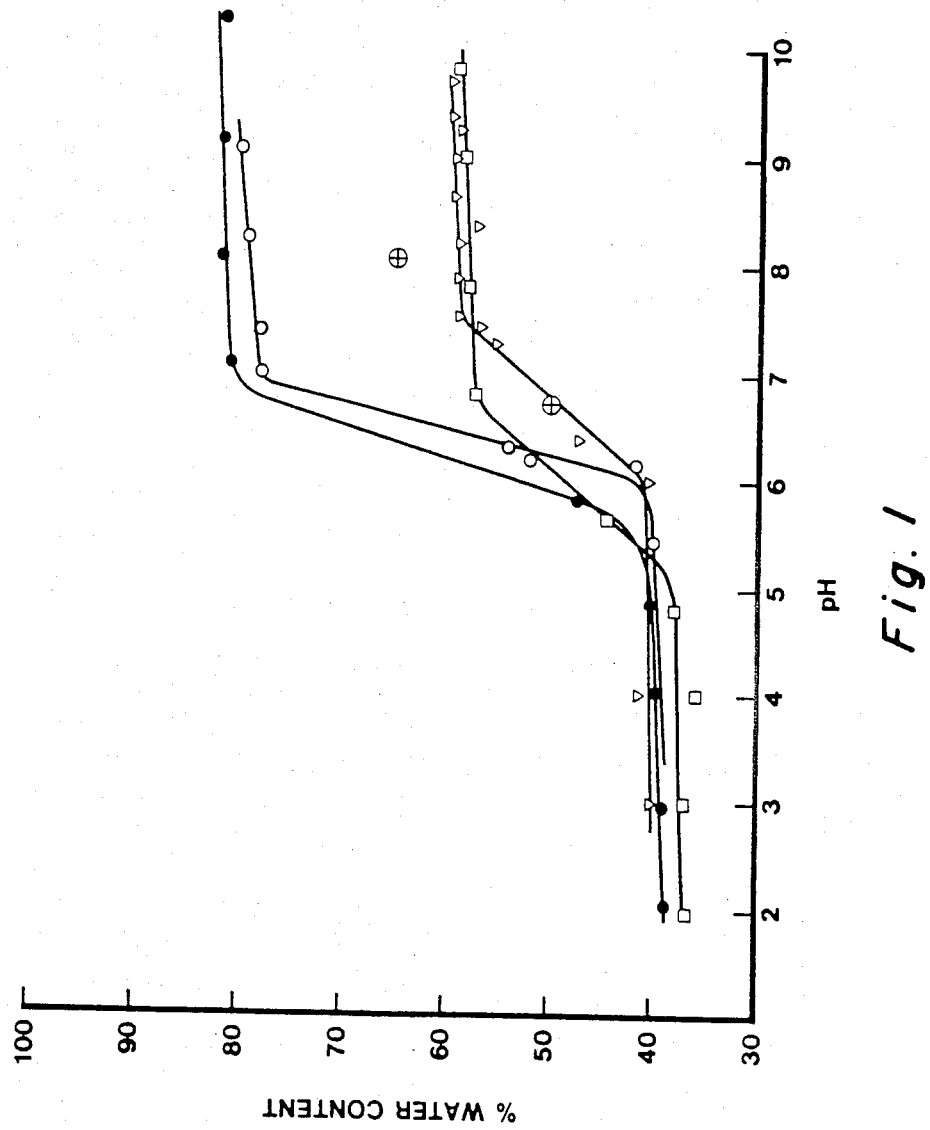
FIG. 1 is a graphical illustration showing how water content of pHEMA/MAA gels varies with the pH of equimolar (0.01) buffered aqueous solutions containing: ● water, ○ urea (9 grams/liter), □NaCl (9 grams/liter), ∇NaCl and urea (each at a concentration of 9 grams/liter); two points ⊕ show swelling in physiological urine.

The invention comprises grafting or surface interpenetrating a thin layer between 50 Å and 1000 microns of a hydrogel which has the capability of shrinking and swelling on the urine-contacting surfaces, for example the interior cavity of an artificial bladder, which is itself fabricated of a polymeric material, such as polyurethane, which displays substantially no physical dimensional alterations in the presence of urine.

The grafted hydrogel should have characteristics which will a priori allow empirical assessment of its shrink/swell behavior and the purity of the starting monomers must therefore be well known. In this regard, HEMA monomer normally contains unknown amounts of impurities of MAA and crosslinker, e.g. ethylene glycol dimethacrylate (EGDMA), which can be comparable to the levels used for doping the pure HEMA monomer. The levels of MAA and EGDMA, as initial impurities, have in fact been found to range from a low of 0.1 mole fraction % of either to highs of about 10% and 3%, respectively. These impurities are by-products from the synthesis of the monomer and/or from subsequent hydrolysis or transesterification of the monomer during transportation and storage. Because the very monomer whose concentration must be controlled might be present as an impurity, it would at best be difficult, and perhaps even impossible, to use HEMA monomer as received and still maintain thorough control over the hydrogel properties.

Therefore, purification steps are performed on all HEMA monomer batches prior to use; the procedure described immediately hereinafter assumes an initial batch size of 200 ml. Methacrylic acid as an impurity may be removed by stirring the monomer with about 15% by weight anhydrous sodium carbonate for a couple of hours at about 24° C., then vacuum filtered through, e.g. two No. 50 Whatman filter papers. The yield on an initial volume of HEMA monomer is about 95%.

The impurity EGDMA may then be removed by first dissolving the MAA-purified monomer in about three times its volume of distilled water. Four liquid-liquid extractions are then performed on the diluted monomer with 50 ml of a 1/1 by volume mixture of carbon tetrachloride and cyclohexane, the layers being allowed to separate for 30 minutes between extractions. Usually, two layers are formed in this extraction step. However, three layers may form if the solvent capacity is exceeded due to an overabundance of impurities. This problem may be circumvented by increasing the solvent-to-aqueous phase ratio. The organic layer containing EGDMA is discarded after each extraction. The aqueous phase is placed under vacuum to remove any remaining organic solvent. The HEMA is then salted out with NaCl, dried with anhydrous sodium sulfate and filtered. This purification step generally has a yield of about 93%.

The partially purified HEMA monomer is then vacuum distilled in the presence of about 1.8 grams of hydroquinone (added to prevent polymerization) at 50 to 80 microns of Hg. The monomer is collected at 38° to 42° C. with the distillation flask being heated in a water bath at 50° to 55° C. The collection flask is cooled in a dry ice/acetone bath. The distillation process proceeds at a rate of about 75 ml/hour. The first and last fractions of the distillation product are discarded. When the distillation is terminated, the pure HEMA is transferred to an opaque glass bottle and stored at 0° C. until use. The yield from the distillation is about 80%, with the overall yield being about 70%.

The purity of the repurified HEMA product may then be determined by high pressure liquid chromatography (HPLC). For example, the inventors use a Varian (trademark of Varian Associates, Palo Alto, Calif.) Model 5000 HPLC equipped with an ultraviolet detector, a 25 cm reverse phase C-18 Ultrasphere-IP column (trademark of Altex, Brownlee Labs, Santa Clara, Calif.), the UV detector wave length being set to 217 nM. The column temperature is allowed to remain at ambient temperature and HPLC grade methanol and water are used as the eluent at a constant (isocratic) ratio of 60 parts methanol to 40 parts water. The flow rate is fixed at about 0.8 ml per minute. All samples are diluted with pure methanol to 1/2000. Ten microliter samples are injected for each analysis. By comparing the peak heights or peak areas as given by, e.g. an electronic integrator, and comparing the peak heights or areas with those exhibited by standards of known concentration, the amount of MAA and EGDMA can be appropriately quantified.

Continuous, thin surfaces of hydrogel can be formed on structural polymers by several methods; these include formation of interpenetrating polymer networks and grafting. Grafting involves the covalent attachment of the hydrogel polymer to the structural polymer. Graft methods for acrylic-based gels generally involve addition polymerization initiated by a free-radical on the structural substrate polymer. The radicals are generally initiated by any of several processes, e.g., ionizing radiation, ultraviolet light, electron beams, ceric ion, and microwave-generated hydrogen ions. Grafting methods are commonly named for the method of generating the radical. Choice of the grafting method depends upon the chemical nature of the substrate material, the geometry to be grafted, and economic factors. For reasons associated with ability to graft internal surfaces, ease of use, and available facilities, the inventors have produced gel coatings on structural (urethane) polymer by the ceric-ion process.

To use the ceric-ion grafting technique, one needs a grafting container made from a material that will not quench free radicals that are formed, i.e., glass or polyethylene. The grafting vessel must be purged of oxygen and have appropriate ports for circulation of solutions over and through the prosthesis to be grafted. It is convenient to use a roller pump to circulate graft solution. The prosthesis must first be thoroughly cleansed (degreased) with detergent and swelling agents, then wet out with distilled water. This cleaning process is effectively performed in an ultrasonic bath at 50° C. The total reaction solution (volume=$T_v$) is composed of $T_v/5$ of reactive polymer precursors, i.e., ultrapure HEMA, the desired mole fraction of MAA and crosslinker (e.g., TEGDMA) and $3T_v/4$ of water. (The remaining fraction of $T_v$ is used to dissolve the graft initiator, cerium ammonium nitrate, at a concentration given by $T_v/120$ (gm/ml) in the remaining volume, $T_v/20$; this solution is used later.)

The large volume of reaction solution is mixed thoroughly and purged of oxygen by bubbling nitrogen gas through it. The reaction solution is then poured into the grafting container with the mounted prosthesis and with a nitrogen flow to maintain an oxygen-purged environment. The reactants are circulated both inside and outside the prosthesis (assuming all surfaces are to be grafted) for a short time. This assures that all surfaces are exposed to monomers and tends to slightly swell the surface, thereby allowing access to more grafting sites. Next, the small, remaining portion of reaction solution ($T_v/20$) is added to the container and circulated to start the reaction which continues, typically for 15 minutes or until the desired thickness of graft is achieved. Internal structures graft evenly only when there is adequate circulation of the reaction solution. The reaction is quenched by dumping the solution and rinsing all surfaces with 50/50 ethylene glycol and distilled water, then with pure distilled water. The solvent/monomer ratio, ceric ion molarity, and type of solvent are useful parameters that can be varied to alter graft thickness and surface appearance. Prior to implantation, toxic ingredients must be leached out; these include residual monomer, oligomer and cerium salts.

The above description represents a typical embodiment of the ceric-ion grafting technique although, of course, variations thereof can certainly be implemented without departing from the scope of the invention. Methodology for ceric-ion grafting is in and of itself well known as from Halpern et al, Natl. Tech. Inform. Ser., #PB-244913/6WV (1976). It will further be appreciated by those skilled in the art that alternative approaches, such as the use of ionizing radiation mentioned above, could advantageously be used to circumvent certain extra steps involved with the ceric-ion technique, such as the need to leach out toxic ingredients.

With good laboratory technique, hydrogel surfaces displaying repeatable behavior are readily made.

It should further be noted that, although a description of grafting has been given, the formulation of the hydrogel layer as a surface interpenetrated polymer is fully equivalent to grafting. The interpenetrated polymer is thought to be formed largely as a physical entanglement of the hydrogel with the surface of a polymeric device as it forms thereon; this is in contrast to grafting, which occurs largely through the polymerizing hydrogel covalently attaching to grafting sites formed by the initiator acting on the device's surface. Thus, to interpenetrate, the device can, for example, be soaked in a hydrogel monomer (e.g. HEMA), advantageously in a solution of the monomer to facilitate swelling and pore-opening on the device's surface, followed by placing the soaked device in a solution containing the remaining monomers used to form the hydrogel copolymer. Polymerization can be initiated, e.g. by ionizing radiation. It should be noted that, probably, neither "grafting" nor "interpenetration" proceeds exclusively via one mechanism or another. The point is that such techniques are equivalent for purposes of this invention regardless of the label by which they are known.

The lower limit of graft thickness for purposes of the invention is a compact, almost monolayer, coat of gel; this would be about 50 to 200 Å thick. A preferred thickness is in the range of 1 to 30 microns when hydrated in acidic, saline solution. An upper level is set by the maintenance of correct apparent sizes for urine flow or storage and to allow for stains that occur on bending or flexure of surfaces, regardless of whether the gel is swollen or shrunken. On this basis, the graft layer is advantageously less than 1 mm thick.

As previously mentioned, the MAA and crosslinker (TEGDMA) must be maintained within reasonably critical concentration ranges to satisfy the polymer physics of the collapse phenomenon while yet maintaining the mechanical integrity of the hydrogel layer.

Advantageously the upper limit of crosslinker in the hydrogel is 0.5 mole fraction %. This uper limit assures that the hydrogel will be able to adapt readily via changes of rubber elasticity to the fair range of stress occasioned by changes in urine composition. Beyond this limit, the ensemble of possible polymer configurations may be greatly limited by additional crosslinking. That is, further crosslinking could very possibly limit the response of the polymer as urine composition changes and thereby inhibit the shrink/swell mechanism by which the hydrogel layer sloughs off calcium scaling.

As crosslinker, tetraethyleneglycol dimethacrylate (TEGDMA) is preferred. Other polyethyleneglycol dimethacrylates, such as mono- or diethyleneglycol dimethacrylate may be used as well, but TEGDMA is preferred due to its better solubility in the aqueous reaction solution.

The lower limit of crosslinker in the hydrogel is set by the effective coverage of the graft process. That is, if one could achieve a dense "grass" of covalently bonded polymer, it might conceptually not be necessary to use a crosslinker. Practically, this ideal conceptual situation is probably not possible and the inventors have found that about 0.01 mole fraction % is a lower limit which yet desirably imparts the minimum structural integrity to the polymer which is practically required.

The range of MAA in the hydrogel is desirably from about 1 to about 3 mole fraction %. To obtain the critical point or collapse effect there must be some ionizable species present, and the inventors have determined that about 1% of MAA is the lower limit at which the collapse is effective to prevent scaling. From this lower limit up to about 3% is preferred as, above 3%, the gel is mechanically very weak and fractures easily in its swollen state such that surface damage becomes a factor which can affect the longevity of the gel, and thus of the grafted or interpenetrated urological device itself.

A particularly advantageous embodiment may be constructed by formulating the gel to contain about 0.15% crosslinker (TEGDMA) and about 2.0 to about 2.5% MAA, the residual being HEMA, and wherein all %'s refer to mole fraction. With this formulation the gel exhibits good mechanical stability and demonstrates shrink/swell behavior which resists or prevents calcification.

The manufacture of structural components for urinary tract prostheses involves the use of common methods known in the art for fabrication of implantable prostheses. In the case of urethane structures, which represent preferred embodiments for use in the present invention, the procedures are similar to those of the artificial heart or ventricular assist devices, e.g., as shown in U.S. Pat. No. 4,131,604, herein incorporated by reference. Alternatively, a polyurethane, such as that described in U.S. Pat. No. 4,131,604 may be dissolved in a good solvent, e.g., dimethyl acetamide, and dipcoated or rotationally cast onto mandrels. Such processes produce a well-defined polymeric structure, whose dimensions and shape are set by the demands on the prosthesis, e.g., a sufficient diameter to allow free flow at low pressures. In the case of an artificial urinary bladder, there are several regions of commonplace geometric form. The urine is transported by a tubular structure, which is commonly inserted into the biological ureter. These tubes empty into a storage region for urine; this region generally changes volume by unfolding or flexure rather than by stretching. The urine is emptied via another tubular structure which has a controlling valve or clamp. Examples of urological prostheses are provided in U.S. Pat. Nos. 4,229,550, 3,953,897 and 3,783,454, all of which are herein incorporated by reference. A urological device for veterinary use is similarly described by U.S. Pat. No. 3,881,199. The present inventors have fabricated structures such as these and successfully grafted them with the copolymer hydrogel.

Implantation tests have also been conducted. For example, a prosthetic ureter grafted with hydrogel and retrieved after 6 months implantation, showed no encrustation or change of mechanical properties.

The swelling and shrinking behavior of the gels containing different MAA and cross-linker content have been explored by placing them in various swelling solutions containing electrolytes and urea at different pH values typical of physiological urine. The exact location and the magnitude of volume changes may be controlled by altering the MAA and cross-linker content in the gel.

FIG. 1 shows the response of a pHEMA/MAA bulk hydrogel doped with 2.5% and 0.15% mole fraction of MAA and TEGDMA, respectively, to different swelling environments. The FIGURE is intended to illustrate the collapse phenomenon with the bulk gel. The swelling environments consisted of water (●), aqueous urea at 9 grams/liter (O), aqueous NaCl at 9 grams/liter (□), an aqueous solution of urea and NaCl, each at 9 grams/liter (∇), and physiological urine ⊕. Each of the preceding liquid environments was buffered to different pH values using equimolar buffering solutions containing 0.01M solute content. The acid buffers that were used include combinations of one or more of the following: HCl, potassium acid phthalate, acetic acid, sodium acetate, potassium phosphate, and sodium hydroxide. The alkali buffers include combinations of one or more of the following: potassium phosphate, sodium tetraborate, sodium carbonate, sodium bicarbonate, and sodium hydroxide.

As FIG. 1 shows, collapse of the gel appears as a dramatic change in volume, described by its water content, 100 (wet wgt.−dry wgt.)/(wet wgt.), versus pH. Gels equilibrated in the different pH solutions, in the absence of urea and salt, demonstrated critical point behavior with the large change in volume occurring between pH 6 and 7. The swollen volume (80% water content) of the gel was approximately six times its shrunken volume (40%). Addition of NaCl (9 grams/liter) to the buffered system lowered the maximum swelling to about 60% water content and decreased the slope of the swelling transition. Gels swollen in combined urea/NaCl solution behaved similarly to those swollen in NaCl solution alone.

Two points showing the effects of urine at two different pH values on the swelling behavior of the gel are also shown in FIG. 1. The point at pH 8.0 was adjusted to this value by addition of a small amount of sodium carbonate to the urine sample at pH 6.5. These points fall in the vicinity of the curve containing urea and NaCl. The swelling of these gels in urine at different pH verifies the fact that gels can be made that are responsive to changes in urine composition. Gels swollen in urine at pH 8.0 are twice as large as gels equilibrated in urine at pH 6.5. The large swelling of the gel, as compared to controlled solutions containing urea and saline, at pH 8.0, may be due to low osmolarity of the urine specimen used in this experiment.

Gels containing ionizable substituents such as MAA at low cross-linker content swell in certain solvents by as much as 3,000% with water contents on the order of 97%. Gels that are made without ionizable groups will not demonstrate this drastic swelling behavior unless, of course, hydrolyzable groups in the polymer are ionized by subsequent hydrolysis, or other degradation processes peculiar to the gel.

Thus, by effecting the collapse phenomenon in conjunction with a thin hydrogel surface, it will be readily appreciated by those skilled in the art how the quick response times to urological changes and, therefore, now urological devices fabricated according to the invention overcome deficiencies inherent in the prior art.

Experiments by the inventors on retrieved implants of artificial ureters and urinary bladders that contained pHEMA in the form of both bulk gels and grafted surfaces indicate that the gels may have contained significant amounts of MAA impurities and were capable of undergoing local deformation in response to the changing urological environment. Some initial work used HEMA monomer as received from chemical suppliers without analysis or further purification. Subsequent HPLC analysis of residual amounts of the HEMA monomer indicated that impurities of MAA and EGDMA as high as 6% and 1%, respectively, may have been initially present in these batches. Swelling tests of sections of explained prosthetic bulk hydrogel ureters revealed that the radial dimensions of the conduit changed by approximately 50% when placed in a basic solution and returned back to their original size in mild acid solution. The low overall amount of swelling may be the result of a large amount of cross-linker present in the gel made from the unpurified monomer starting materials (between 0.5 and 1%), and hence emphasizes the need for initial purification. Hydrogel ureters of this nature, however, remained patent in the urinary tract for periods of up to three years. In the case of hydrogel grafted prosthetic urinary bladders, short term tests (6 weeks) showed that hydrogel grafted surfaces resist calcium encrustation even in the presence of infected urine. Microscopic examination of the hydrogel surface after autopsy revealed a surface structure that was swollen in thickness by as much as 400% as compared to non-implanted controls.

The nature of calcification resistance in the biological urinary tract is not well understood. However, it is interesting to note that the entire tract is lined with a layer of mucopolysaccharides, which are ionically charged gel-like substances containing large amounts of imbibed water. Structures made with pHEMA gels interfacing urine may perform similar functions as these mucopolysaccharides. Thus, physiochemical properties and processes are critical to the design of urinary biomaterials and prostheses as are simple chemical structure and physical properties.

Several factors in addition to the sloughing mechanism may influence the calcification resistance of hydrogels in the urinary tract, although the inventors in no way wish to be bound by these theories. These factors are likely to differ in levels of importance from those for similar gels implanted in physiologically controlled sites, for example, as in osteogenesis (Smahel et al, Acta Chirurgiae Plasticea, 13, 193, 1971) or reconstructive surgery (Sprinel et al, J. Biomed. Mater. Res., 7, 123, 1973), In most of the body the environment of the gel is very stable and the chemical inertness of the gel is a key factor. However, the ability of the gel to respond to local environmental changes by shrinking or swelling may be related to events that effect its patency in the urinary tract. While gels are somewhat chemically inert, they are not physically inert. The water content of pHEMA-based hydrogels is normally about 40%. When the gel is swollen a few hundred percent, the water content increases to around 80%. This large water content may enhance the action as an interface of water (Andrade et al, *Hydrogels for Medical and Related Applications*, Ed. J. D. Andrade, A.C.S. Symp. Series. No. 31, Washington, D.C., 1976) and prevent precipitates from nucleating on the gel wall. The tensile strength of the gel also decreases as it imbibes water. Krindel and Silberberg show that for certain flow rates, gel tubes can have a higher hydrodynamic resistance to flow than rigid tubes (J. Coll. Interface. Sci., 71, 39, 1979). Via dimensional analysis of the resistance data, they connect this behavior with the elasticity of the gel and hypothesize an irregular motion at the gel-liquid surface. Swollen gels, with their lower modulus of elasticity, will allow ripples to form more readily on their surfaces than shrunken gels and thus may prevent calcium salt precipitates from adhering to the gel wall or dislodge small precipitates as they are formed.

The interrelationship of urea, swelling and calcium solubility is suggestive of another mechanism for calcification resistance in the urinary tract. The hydrogel has the potential to function as a replenishable reservoir of urea. Urea in turn is known to help solubilize calcium salts and therefore may prevent precipitates containing calcium from forming on or near the gel wall.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A physiologically compatible urological prosthesis having a urine-contacting hydrogel copolymer surface of a thickness between about 50 Å and 1 mm, said hydrogel copolymer comprising between about 1 and about 3 mole fraction % of methacrylic acid and between about 0.01 and 0.5 mole fraction % of a crosslinking agent, wherein the remainder is 2-hydroxyethyl methacrylate.

2. The prosthesis of claim 1 wherein said coating is between about 1 and about 30 microns thick.

3. The prosthesis of claim 1 wherein said prosthesis has been fabricated from a material comprising polyurethane.

4. The prosthesis of claim 1 wherein said crosslinking agent in said hydrogel copolymer surface is tetraethyleneglycol dimethacrylate.

5. The prosthesis of claim 1 wherein said methacrylic acid is present in said hydrogel copolymer surface in an amount between about 2 and about 2.5 mole fraction %.

6. A process for making a urine-contacting physiological compatible article, comprising the steps of:
   A. purifying 2-hydroxyethyl methacrylate;
   B. adding to said purified 2-hydroxyethyl methacrylate a solvent and from between about 1 and about 3 mole fraction % of methacrylic acid and from between about 0.01 and about 0.5 mole fraction % of a crosslinking agent to form a solution;
   C. forming a hydrogel coating on the urine-contacting surface of a polymeric urological prosthesis by exposing said device to said solution and causing a hydrogel copolymer comprising said 2-hydroxyethyl methacrylate, said methacrylic acid, and said crosslinking agent to form thereon.

7. The process of claim 6 wherein said coating is between about 50 Å and about 1 mm thick.

8. The process of claim 7 wherein said coating is between about 1 and about 30 microns thick.

9. The process of claim 6 wherein said prosthesis comprises polyurethane.

10. The process of claim 6 wherein said crosslinking agent is tetraethyleneglycol dimethacrylate.

11. The process of claim 6 wherein said crosslinking agent is present in an amount between about 0.01 and about 0.5 mole fraction % relative to said copolymer.

12. The process of claim 6 wherein said methacrylic acid is present in an amount between about 1 and about 3 mole fraction % relative to said copolymer.

13. The process of claim 12 wherein said methacrylic acid is present in an amount between about 2 and about 2.5 mole fraction % based relative to said copolymer.

14. The process of claim 6 wherein said solvent is water.

15. A physiologically compatible article comprising a polymeric urological prosthesis having a urine-contacting surface coating grafted or interpenetrated thereon, wherein said surface coating comprises a copolymer, said article being formed by:
   A. purifying 2-hydroxyethyl methacrylate;
   B. adding to said purified 2-hydroxyethyl methacrylate a solvent and from between about 1 and about 3 mole fraction % of methacrylic acid and a crosslinking agent to form a solution;
   C. forming a hydrogel coating on the surface of said polymeric urological prosthesis by exposing said prosthesis to said solution and causing a hydrogel copolymer comprising said 2-hydroxyethyl methacrylate, said methacrylic acid, and said crosslinking agent to form thereon.

16. The process of claim 15 wherein said coating is between about 50 Å and about 1 mm thick.

17. The process of claim 16 wherein said coating is between about 1 and about 30 microns thick.

18. The process of claim 15 wherein said prosthesis comprises polyurethane.

19. The process of claim 15 wherein said crosslinking agent is tetraethyleneglycol dimethacrylate.

20. The process of claim 15 wherein said crosslinking agent is present in an amount between about 0.01 and about 0.5 mole fraction %.

21. The process of claim 15 wherein said methacrylic acid is present in an amount between about 1 and about 3 mole fraction % relative to said copolymer.

22. The process of claim 21 wherein said methacrylic acid is present in an amount between about 2 and about 2.5 mole fraction % based relative to said copolymer.

23. The process of claim 15 wherein said solvent is water.

* * * * *